(12) United States Patent
Wang et al.

(10) Patent No.: US 11,523,734 B2
(45) Date of Patent: Dec. 13, 2022

(54) VAGINAL SPECULUM

(71) Applicant: Frog Design Inc., San Francisco, CA (US)

(72) Inventors: Frances Wang, San Francisco, CA (US); Ryan Starling, San Rafael, CA (US); Scott Thibeault, Redwood City, CA (US); Rachel Hobart, San Francisco, CA (US)

(73) Assignees: Yona Care, LLC, Dover, DE (US); Frances Wang, San Francisco, CA (US); Rachel Hobart, Eugene, OR (US)

( * ) Notice: Subject to any disclaimer, the term of this patent is extended or adjusted under 35 U.S.C. 154(b) by 231 days.

(21) Appl. No.: 17/091,009

(22) Filed: Nov. 6, 2020

(65) Prior Publication Data

US 2022/0142465 A1  May 12, 2022

(51) Int. Cl.
*A61B 1/303* (2006.01)
*A61B 1/32* (2006.01)
*A61B 1/00* (2006.01)

(52) U.S. Cl.
CPC .......... *A61B 1/303* (2013.01); *A61B 1/00147* (2013.01); *A61B 1/32* (2013.01)

(58) Field of Classification Search
CPC ........... A61B 1/303; A61B 1/32; A61B 1/105; A61B 1/103
See application file for complete search history.

(56) References Cited

U.S. PATENT DOCUMENTS

| | | | | |
|---|---|---|---|---|
| 361,087 | A * | 4/1887 | Schenck | A61B 1/32 600/211 |
| 2,374,863 | A * | 5/1945 | Guttmann | A61B 1/32 600/224 |
| 3,789,829 | A * | 2/1974 | Hasson | A61N 5/1016 600/221 |
| 6,048,308 | A * | 4/2000 | Strong | A61B 1/303 600/222 |
| 6,280,379 | B1 * | 8/2001 | Resnick | A61B 1/32 600/220 |
| 7,371,212 | B2 * | 5/2008 | Klaassen | A61B 1/32 600/222 |
| 2017/0181615 | A1 * | 6/2017 | Vella | A61B 1/303 |

\* cited by examiner

*Primary Examiner* — Kevin T Truong
*Assistant Examiner* — Tracy L Kamikawa
(74) *Attorney, Agent, or Firm* — Harrington & Smith

(57) ABSTRACT

A speculum includes a handle; a lower leaf extending forward and distally from the handle; at least one upper leaf supported on the handle; a lever pivotally coupled to the handle; and a pin extending from the lever and slidably coupled to the at least one upper leaf. Movement of the lever relative to the handle causes the lever to slide the pin and pivotally move the at least one upper leaf relative to the lower leaf from a collapsed position to an open position.

18 Claims, 6 Drawing Sheets

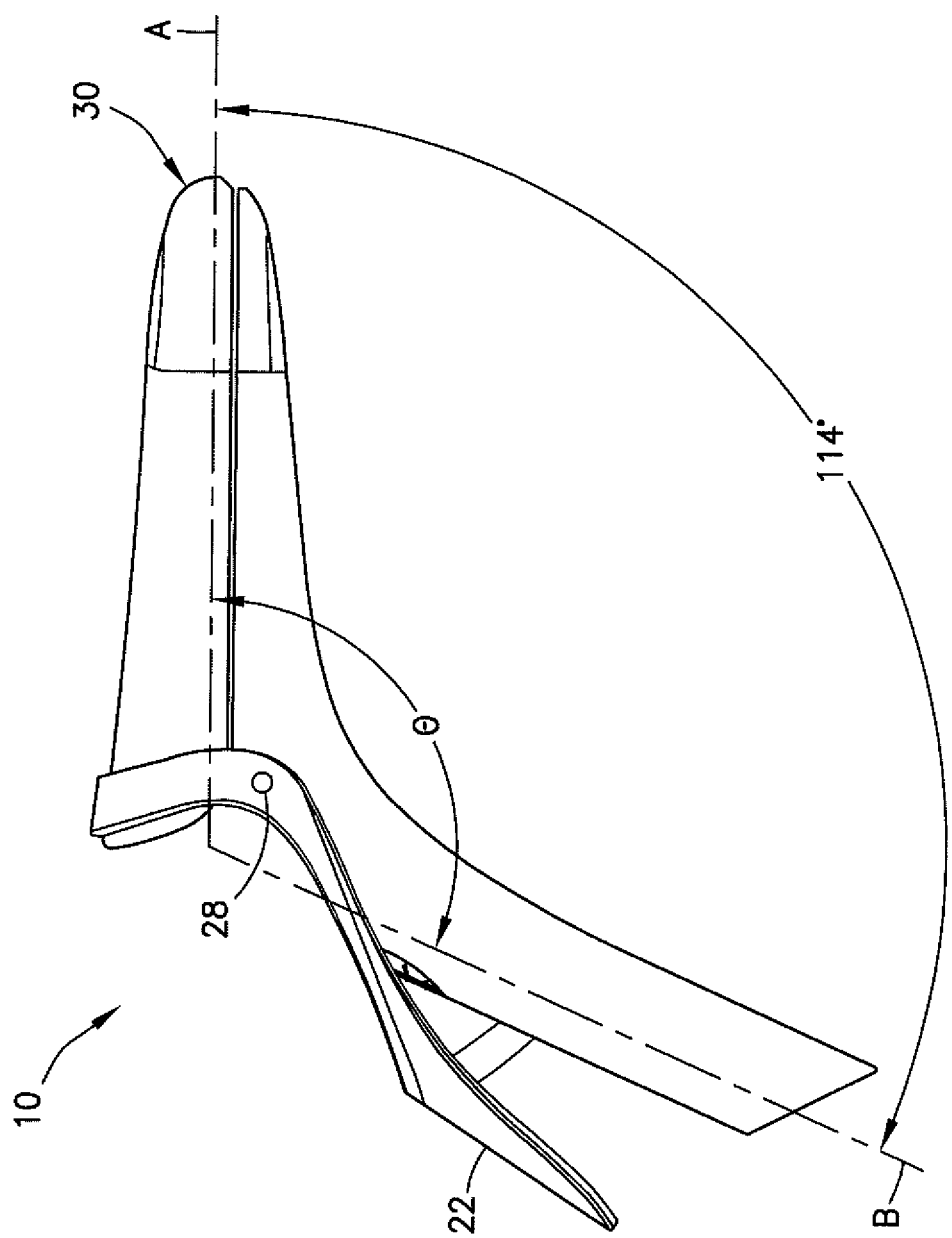

VAGINAL SPECULUM

BACKGROUND

Technical Field

The exemplary and non-limiting embodiments described herein relate generally to handheld medical devices. The exemplary and non-limiting embodiments described herein relate more particularly to a vaginal speculum.

Brief Description of Prior Developments

Vaginal specula are devices used in the field of gynecology for the pelvic examination of patients with vaginas. A vaginal speculum generally has a handle with a lever, the manipulation of which causes blades to move in opposing directions to dilate the walls of a vagina thus allowing for the examination of the cervix of the patient.

SUMMARY

In accordance with one aspect of the invention, a speculum comprises a handle; a lower leaf extending forward and distally from the handle; at least one upper leaf supported on the handle; a lever pivotally coupled to the handle; and a pin extending from the lever and slidably coupled to the at least one upper leaf. Movement of the lever relative to the handle causes the lever to slide the pin and pivotally move the at least one upper leaf relative to the lower leaf from a collapsed position to an open position.

In accordance with another aspect of the invention, a vaginal speculum comprises: a handle graspable by a user and having a lower leaf distally extending from a forward end; a first upper leaf hingedly coupled to the handle and extending along the lower leaf; a second upper leaf hingedly coupled to the handle and extending along the lower leaf; a lever pivotally coupled to the handle; and a pin extending from the lever, the pin having a first end slidably engaged with the first upper leaf and a second end slidably engaged with the second upper leaf. The lower leaf, the first upper leaf, and the second upper leaf are configured in a collapsed position to be inserted into a patient. Movement of the lever relative to the handle causes the lever to slide the first end of the pin and the second end of the pin to pivot the first upper leaf and the second upper leaf, respectively, away from the lower leaf and to an open position.

In accordance with another aspect of the invention, a medical device comprises: a handle graspable by a user and having a lower leaf extending from a forward end thereof to a distal end; a lever pivotally coupled to the handle; at least one upper leaf hingedly coupled to the handle and pivotable relative to the handle using the lever; and a lock operably coupled to the handle and the lever. The lock comprises a post depending from the lever and extending through a hole and into the handle, a torsion spring having a first end and a second end and retained on the post by tension of the torsion spring and inhibiting movement of the post and lever relative to the handle, and a wedge configured to engage the first end and the second end of the torsion spring upon movement of the wedge to release the tension of the torsion spring and allow movement of the post and lever relative to the handle. The lower leaf and the at least one upper leaf, in a collapsed configuration, are configured to be inserted into a vagina of a patient, expanded, and locked into an open position or the collapsed position using the lock.

BRIEF DESCRIPTION OF THE DRAWINGS

The foregoing aspects and other features of the invention are explained in the following description, taken in connection with the accompanying drawings, wherein:

FIG. 2 is a side view of the speculum of FIG. 1;

DETAILED DESCRIPTION OF EMBODIMENTS

Figure 1:
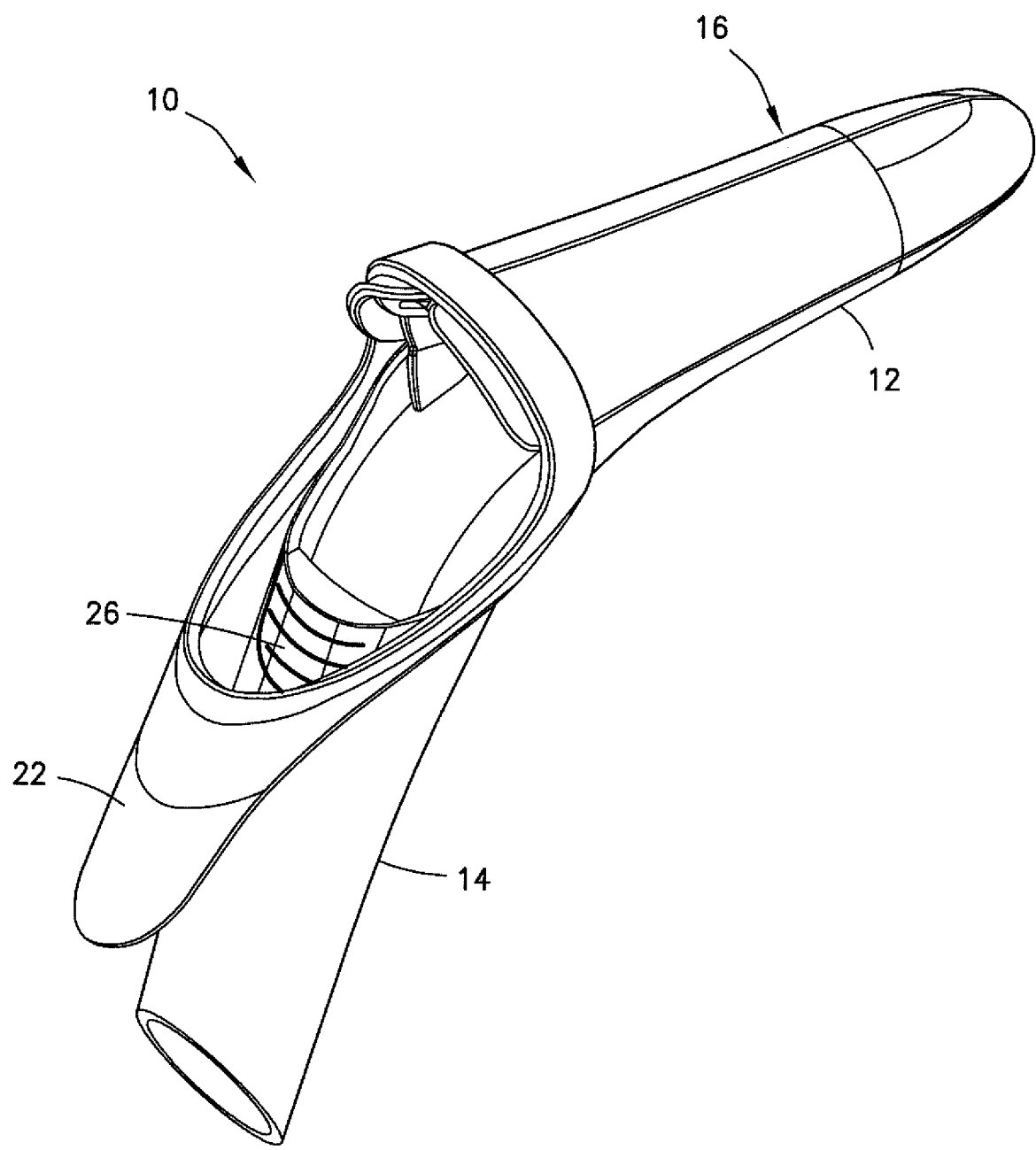
FIG. 1 is a perspective view of one exemplary embodiment of a vaginal speculum.

Referring to FIG. 1, a vaginal speculum is shown generally at 10 and is hereinafter referred to as "speculum 10." Although the features will be described with reference to the exemplary embodiment shown in the drawings, it should be understood that features can be embodied in many alternate forms of embodiments. In addition, any suitable size, shape, or type of elements or materials could be used.

In the exemplary embodiment of FIG. 1, the speculum 10 comprises a lower leaf 12 having a handle 14 fixedly depending from a proximal (rearward) end of the lower leaf 12, a two-piece upper leaf 16, and a lever 22. The handle 14 may be hollow to allow suitable structure for drainage, illumination, or the like, to be incorporated. The lever 22 is pivotally coupled to the handle 14 approximately at the proximal end of the lower leaf 12. The two-piece upper leaf 16 is hingedly supported on the handle 14 (for example, by a portion of a hoop, shown below at 30 in FIG. 4) disposed on the proximal end of the lower leaf 12. A button or slider 26 is positioned on a top side the handle 14 and is configured to be operated by a thumb of a user, thus allowing for control of locking the pieces of the upper leaf 16 in an open position or a closed position and unlocking of the pieces of the upper leaf 16 to collapse the upper leaf 16 while reducing fatigue and strain on the thumb itself.

Referring to FIG. 2, the lever 22 is pivotally coupled to the handle 14 at a pivot point 28. The lever 22 is ergonomic and centered relative to the handle 14 to allow for ambidextrous use. As can be seen, the speculum 10, in a configuration in which the two-piece upper leaf 16 and the lower leaf 12 are closed, approximates a tapered cylindrical shape having a substantially rounded nose 30 with the surfaces of the two-piece upper leaf 16 and the lower leaf 12 curving sufficiently to define a blunted or rounded front end. This tapered cylindrical shape may facilitate the insertion of a distal (forward) end of the speculum 10 and eliminate or at least minimize the need to turn the speculum 10 during use.

An angle θ from an axis A extending through the insertion end of the speculum 10 defined by the upper leaf 16 and the lower leaf 12 relative to an axis B extending through the handle 14 may be about 114 degrees. The angle θ may be anywhere between about 90 degrees and about 130 degrees. This angle θ generally creates a space between the user's fingers when positioned on the handle 14 and the patient's body.

Figure 3B:
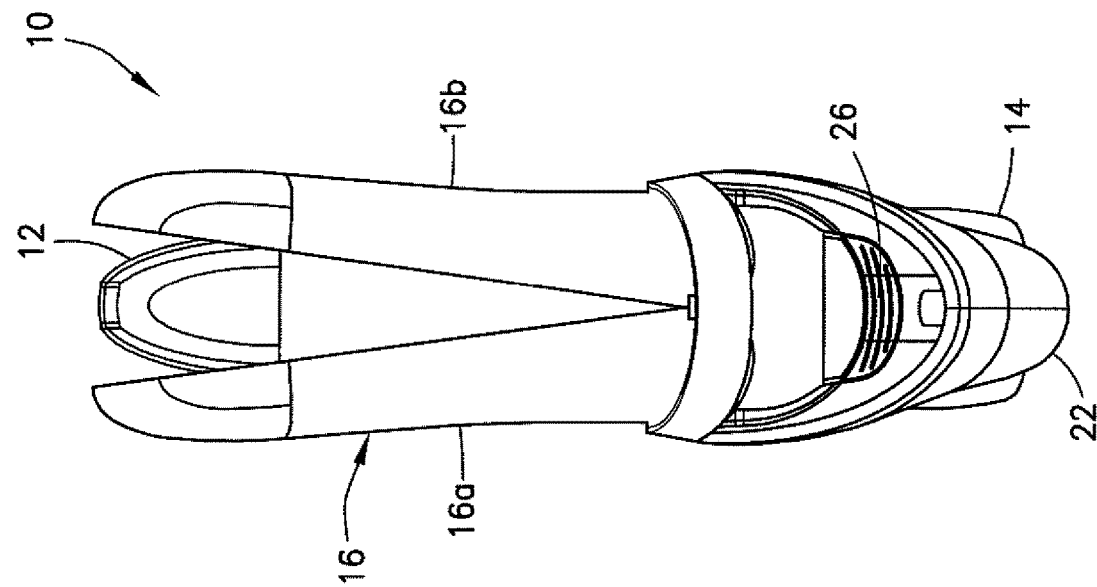
FIG. 3B is a top view of the speculum of FIG. 1 in an open configuration.
Figure 3A:
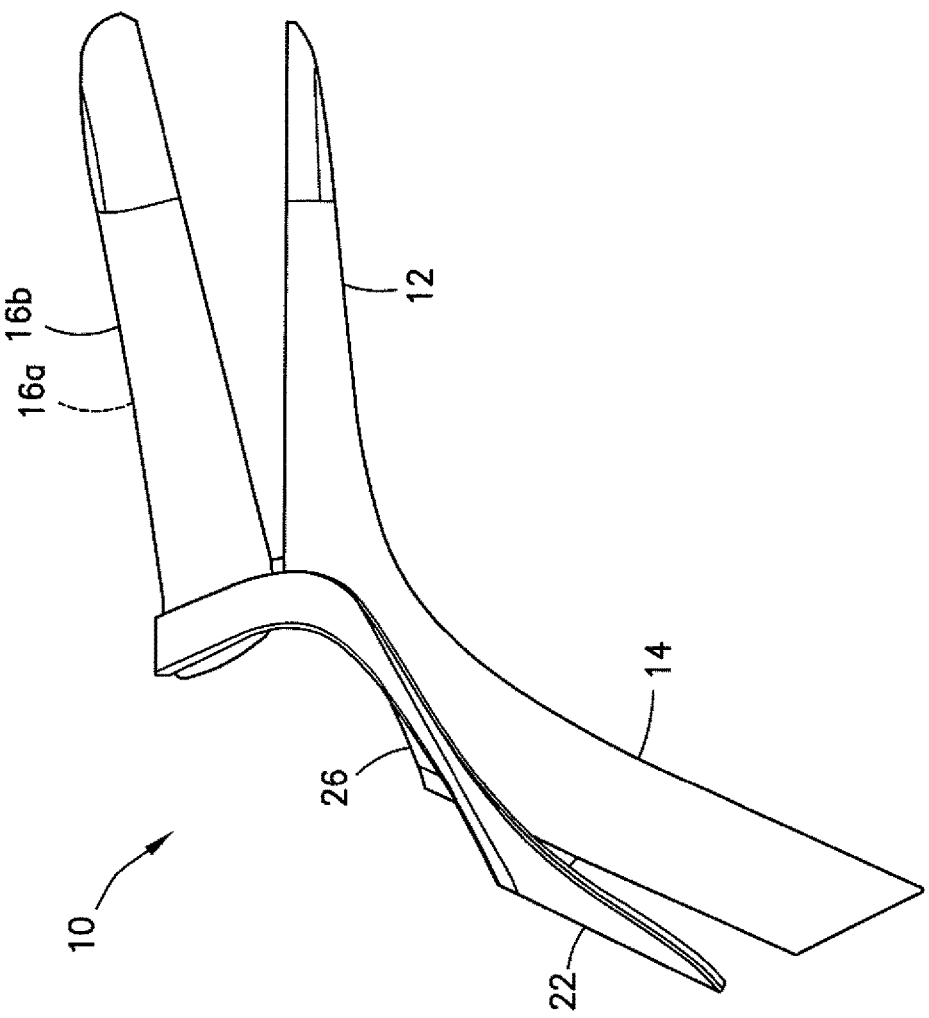
FIG. 3A is a side view of the speculum of FIG. 1 in an open configuration.

Referring to FIGS. 3A and 3B, the speculum 10 is shown in an "open" position. As shown, the two-piece upper leaf 16 has a first upper leaf 16a and a second upper leaf 16b both of which open upwards and laterally outwards (relative to axis A) at a predetermined angle to reduce tissue collapse and to avoid pressure on sensitive organs anterior to the vagina. Additionally, using the lower leaf to press down towards the posterior of the vaginal entrance may cause the vaginal muscles to relax, which may improve comfort in the patient and ease of insertion of the speculum 10.

Figure 4:
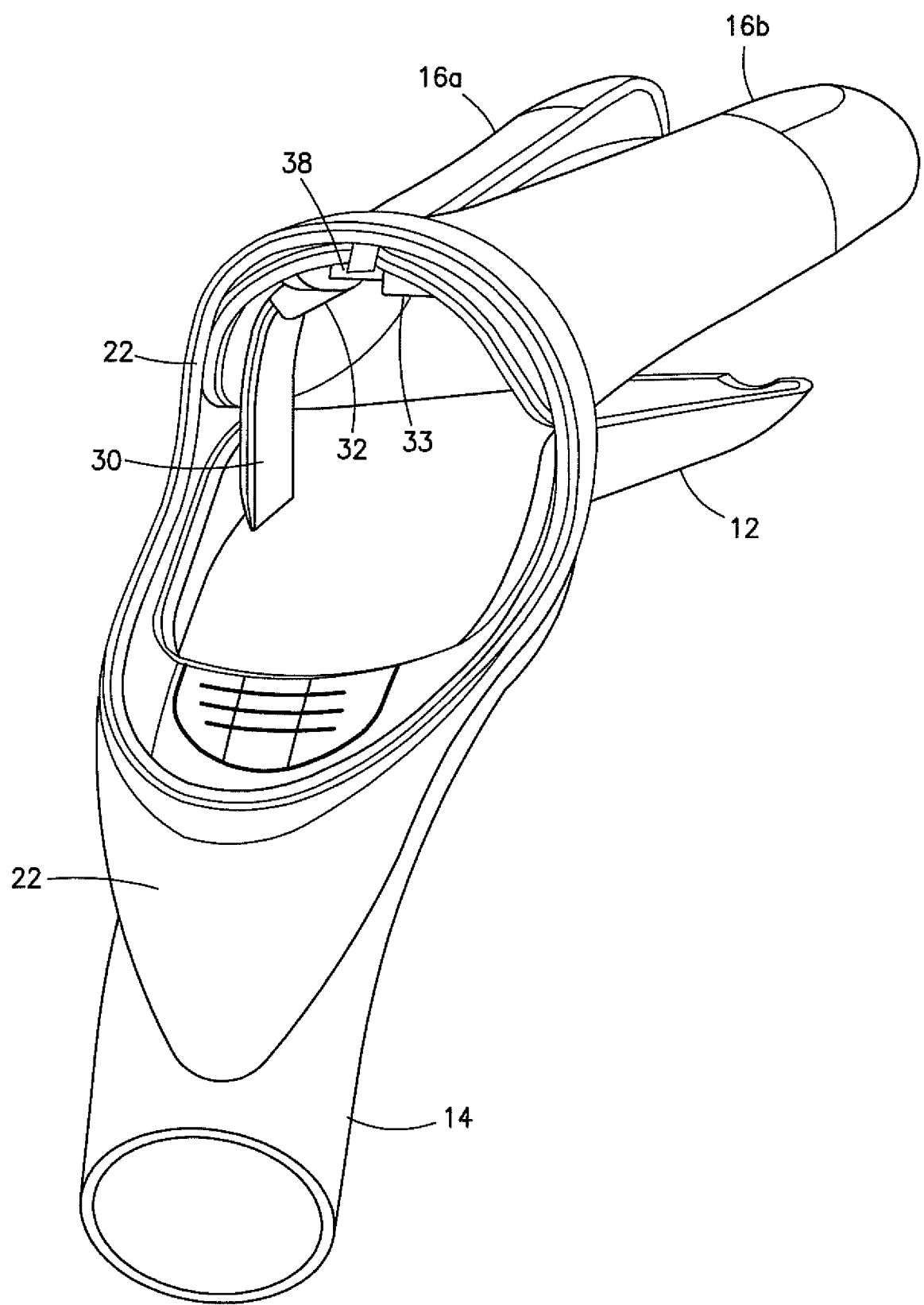
FIG. 4 is a perspective view of the speculum in an open configuration showing hinged and supported upper leaves.

Referring to FIG. 4, the first upper leaf 16a and the second upper leaf 16b may be hinged on and supported by the hoop 30, ends of which are attached or coupled proximate to the area from which the handle 14 depends from the lower leaf 12. This hinged and supported coupling of the upper leaves 16a, 16b to the hoop 30 is effected using hinges 32 and 33.

Figure 5:
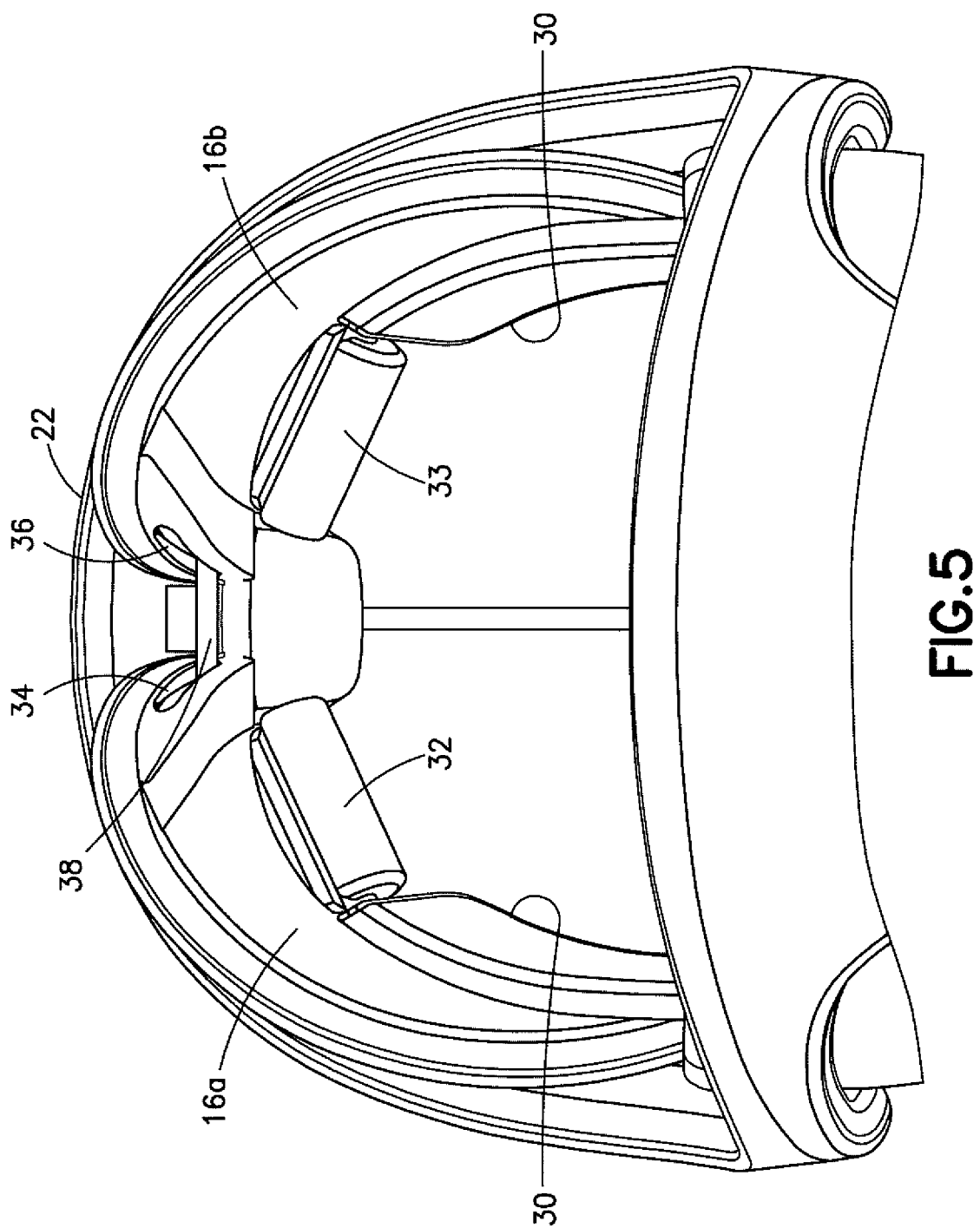
FIG. 5 is a rear view of one example of the speculum showing hinges coupling upper leaves to a support.

Referring to FIG. 5, the first upper leaf 16a has a first slot 34 extending along a portion of an upper and inner edge of the first upper leaf 16a, with the second upper leaf 16b having a second slot 36 extending along a portion of an upper and inner edge of the second upper leaf 16b. The first slot 34 and the second slot 36 are similar, and when the first upper leaf 16a and the second upper leaf 16b are hingedly attached and arranged and assembled on the hoop 30, the openings of the first slot 34 and the second slot 36 face each other. A pin 38 depends from an underside of the lever 22 and is attached at a middle portion thereof such that ends of the pin 38 extend outwardly therefrom. The location of the ends of the pin 38 in the first slot 34 and the second slot 36 in relation to the hinge axes through the respective hinges 32, 33 pulls the upper leaves 16a, 16b open or allows them to close.

Each end of the pin 38 is received into the corresponding first slot 34 or second slot 36 and is configured to slide forward and backward within the slots 34, 36 upon movement of the lever 22. Manipulation of the lever 22 and handle 14 in a squeezing motion causes the upper part of the lever 22 to move in the proximal direction toward the user, which moves the ends of the pin 38 in each slot 34, 36, for example, by pulling the ends of the pin 38 against a terminus of each slot and/or driving the ends of the pin 38 against walls of each slot in arcing motion, thus causing the upper leaves 16a, 16b to pivot on the respective hinges 32, 33 to open the speculum 10. Releasing the handle 14 causes the upper part of the lever 22 to move away from the user, which drives or causes the ends of the pin 38 to move forward in the slots 34, 36, thus allowing the speculum 10 to close.

Figure 6:
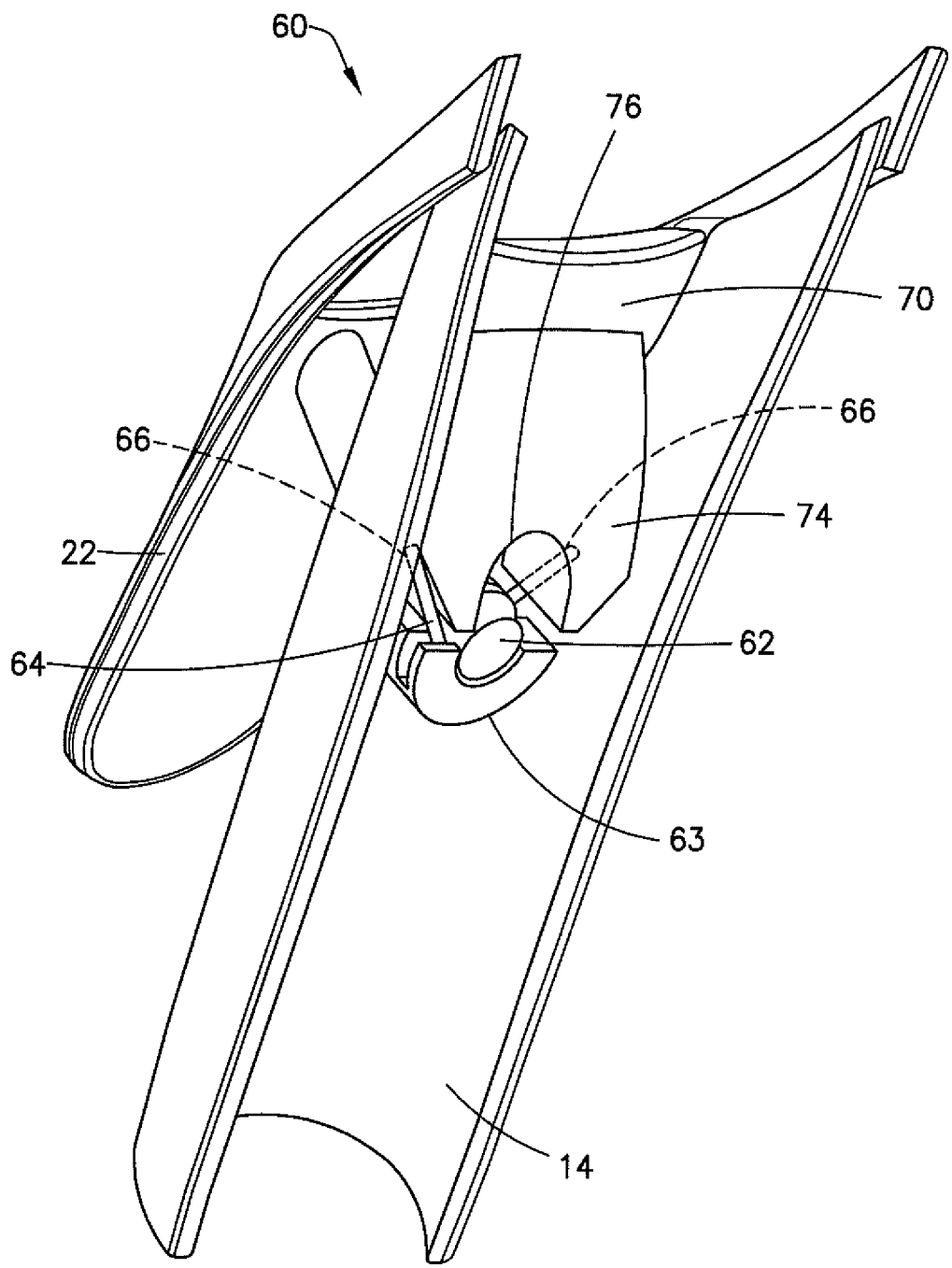
FIG. 6 is a perspective view of one example of a lock for use with the speculum.

Referring to FIG. 6, a mechanism for locking the speculum 10 into an open position is shown generally at 60 and is hereinafter referred to as "lock 60." The lock 60 comprises a post 62 depending from an underside of the lever 22 and extending into or through the handle 14. A torsion spring 64 is wound around the post 62 and retained thereon by tension. The torsion spring 64 may also be retained on the post 62 by being held in a notch in a channel, hole, or other opening through which the post 62 extends. In one exemplary embodiment, the torsion spring 64 may also be held and retained on the post 62 using a support 63. Ends 66 of the torsion spring 64 extend forward (in the direction of the distal end of the handle 14) and urge the button 26 in a direction such that the torsion spring 64 remains tensioned, thereby causing a default position of the speculum 10 to be locked.

The button 26 is accessible to the user's finger or thumb without interference from the lever 22. The button 26 is coupled to or integrally formed with a wedge 74, the wider end of which includes a cutout or slot 76 configured to receive at least a portion of the length of torsion spring 64 wound around the post 62.

In one exemplary operation of the lock 60, the button 26 is moved in the distal direction around a pivot point such that the wedge 74 moves in the proximal direction to wedge open the ends 66 of the torsion spring 64 (taking the speculum 10 out of the default position), thus increasing the cross-sectional diameter of the torsion spring 64 and allowing the post 62 to move freely through the torsion spring 64. The lever 22 may then be squeezed to drive the pin 38 rearward or in the proximal direction in the slots 34, 36, thereby pivoting the upper leaves 16a, 16b on their respective hinges 32, 33 and hingedly opening the speculum 10. Upon moving the button 26 backwards or allowing the ends 66 of the torsion spring 64 to urge the wedge 74 forward in the distal direction (back into the default position), the torsion spring 64 tightens around the post 62. Causing or allowing the torsion spring 64 to tighten holds the post 62 (and the lever 22 and accordingly the leaves 16a, 16b) in the open position. To close the leaves, the user moves the button 26 in the distal direction to drive the ends 66 in the open thereby loosening the torsion spring 64, which allows the post 62 to again move freely out of the handle 14 such that the lever 22 closes and the leaves 16a, 16b collapse to a closed position.

In any embodiment, a material from which the speculum 10 and/or portions of the speculum 10 may be fabricated includes, but is not limited to, stainless steel encased or coated with surgical silicone. The use of stainless steel may provide weight that facilitates the handling of the speculum 10 by the user, and the use of silicone may reduce friction upon insertion of the speculum 10. The use of silicone may also reduce temperature shock to the patient.

In one exemplary embodiment, a speculum comprises a handle; a lower leaf extending forward and distally from the handle; at least one upper leaf supported on the handle; a lever pivotally coupled to the handle; and a pin extending from the lever and slidably coupled to the at least one upper leaf. Movement of the lever relative to the handle causes the lever to slide the pin and pivotally move the at least one upper leaf relative to the lower leaf from a collapsed position to an open position.

The pin may be slidably engaged with the at least one upper leaf by engagement of the pin with a slot in the at least one upper leaf. The at least one upper leaf may be supported on the handle by being hingedly coupled to a portion of a hoop extending from the handle. The at least one upper leaf may comprise a first leaf half and a second leaf half, wherein movement of the first leaf half and the second leaf half to the open position may comprise pivotally moving the first leaf half and the second leaf half upward and laterally outward relative to the lower leaf. The speculum may further comprise a lock on the handle, the lock being configured to maintain the at least one upper leaf and the lower leaf in the open position or the collapsed position. At least the lower leaf and the at least one upper leaf may be fabricated from stainless steel and coated with silicone.

In another exemplary embodiment, a vaginal speculum comprises: a handle graspable by a user and having a lower leaf distally extending from a forward end; a first upper leaf hingedly coupled to the handle and extending along the lower leaf; a second upper leaf hingedly coupled to the handle and extending along the lower leaf; a lever pivotally coupled to the handle; and a pin extending from the lever, the pin having a first end slidably engaged with the first upper leaf and a second end slidably engaged with the second upper leaf. The lower leaf, the first upper leaf, and the second upper leaf are configured in a collapsed position to be inserted into a patient. Movement of the lever relative to the handle causes the lever to slide the first end of the pin and the second end of the pin to pivot the first upper leaf and the second upper leaf, respectively, away from the lower leaf and to an open position.

The first end of the pin may be slidably engaged with the first upper leaf via engagement with a first slot, and the second end of the pin may be slidably engaged with the second upper leaf via engagement with a second slot. The movement of the lever relative to the handle to cause the lever to slide the first end of the pin and the second end of the pin may comprise causing the first end and the second end to engage the first slot and the second slot to pivot the first upper leaf and the second upper leaf, respectively. Each of the first upper leaf and the second upper leaf may be supported on the handle by being hingedly coupled to a portion of a hoop extending from the handle. The vaginal speculum may further comprise a lock on the handle, the lock being configured to maintain the first upper leaf and the second upper leaf in the open position or the collapsed position relative to the lower leaf. At least the lower leaf and the at least one upper leaf may be fabricated from stainless steel and coated with silicone.

In another exemplary embodiment, a medical device comprises: a handle graspable by a user and having a lower leaf extending from a forward end thereof to a distal end; a lever pivotally coupled to the handle; at least one upper leaf hingedly coupled to the handle and pivotable relative to the handle using the lever; and a lock operably coupled to the handle and the lever. The lock comprises a post depending from the lever and extending through a hole and into the handle, a torsion spring having a first end and a second end and retained on the post by tension of the torsion spring and inhibiting movement of the post and lever relative to the handle, and a wedge configured to engage the first end and the second end of the torsion spring upon movement of the wedge to release the tension of the torsion spring and allow movement of the post and lever relative to the handle. The lower leaf and the at least one upper leaf, in a collapsed configuration, are configured to be inserted into a vagina of a patient, expanded, and locked into an open position or the collapsed position using the lock.

The medical device may further comprise a button configured for the movement of the wedge to wedge open the first end and the second end of the torsion spring. The button may be operably coupled to the wedge. The button may be integrally formed with the wedge. The wedge may include a slot configured to receive the post and the torsion spring retained on the post upon the sliding movement of the wedge to release the tension of the torsion spring. The lever may include a pin configured to engage a slot in the at least one upper leaf, wherein movement of the pin in the slot pivots the at least one upper leaf relative to the handle.

It should be understood that the foregoing description is only illustrative. Various alternatives and modifications can be devised by those skilled in the art. For example, features recited in the various dependent claims could be combined with each other in any suitable combination(s). In addition, features from different embodiments described above could be selectively combined into a new embodiment. Accordingly, the description is intended to embrace all such alternatives, modifications, and variances which fall within the scope of the appended claims.

What is claimed is:

1. A speculum, comprising:
   a handle;
   a lower leaf extending forward and distally from the handle;
   at least one upper leaf supported on the handle;
   a lever pivotally coupled to the handle; and
   a pin extending from the lever and slidably coupled to the at least one upper leaf;
   wherein movement of the lever relative to the handle causes the lever to slide the pin and pivotally move the at least one upper leaf relative to the lower leaf from a collapsed position to an open position.

2. The speculum of claim 1, wherein the pin is slidably engaged with the at least one upper leaf by engagement of the pin with a slot in the at least one upper leaf.

3. The speculum of claim 1, wherein the at least one upper leaf is supported on the handle by being hingedly coupled to a portion of a hoop extending from the handle.

4. The speculum of claim 1, wherein the at least one upper leaf comprises a first leaf half and a second leaf half, wherein movement of the first leaf half and the second leaf half to the open position comprises pivotally moving the first leaf half and the second leaf half upward and laterally outward relative to the lower leaf.

5. The speculum of claim 1, further comprising a lock on the handle, the lock being configured to maintain the at least one upper leaf and the lower leaf in the open position or the collapsed position.

6. The speculum of claim 1, wherein at least the lower leaf and the at least one upper leaf are fabricated from stainless steel and coated with silicone.

7. A vaginal speculum, comprising:
   a handle graspable by a user and having a lower leaf distally extending from a forward end;
   a first upper leaf hingedly coupled to the handle and extending along the lower leaf;
   a second upper leaf hingedly coupled to the handle and extending along the lower leaf;
   a lever pivotally coupled to the handle; and
   a pin extending from the lever, the pin having a first end slidably engaged with the first upper leaf and a second end slidably engaged with the second upper leaf;
   wherein the lower leaf, the first upper leaf, and the second upper leaf are configured in a collapsed position to be inserted into a patient; and
   wherein movement of the lever relative to the handle causes the lever to slide the first end of the pin and the second end of the pin to pivot the first upper leaf and the second upper leaf, respectively, away from the lower leaf and to an open position.

8. The vaginal speculum of claim 7, wherein the first end of the pin is slidably engaged with the first upper leaf via engagement with a first slot, and wherein the second end of the pin is slidably engaged with the second upper leaf via engagement with a second slot.

9. The vaginal speculum of claim 8, wherein the movement of the lever relative to the handle to cause the lever to slide the first end of the pin and the second end of the pin comprises causing the first end and the second end to engage the first slot and the second slot to pivot the first upper leaf and the second upper leaf, respectively.

10. The vaginal speculum of claim 7, wherein each of the first upper leaf and the second upper leaf is supported on the handle by being hingedly coupled to a portion of a hoop extending from the handle.

11. The vaginal speculum of claim 7, further comprising a lock on the handle, the lock being configured to maintain the first upper leaf and the second upper leaf in the open position or the collapsed position relative to the lower leaf.

12. The vaginal speculum of claim 7, wherein at least the lower leaf and the first upper leaf and the second upper leaf are fabricated from stainless steel and coated with silicone.

13. A medical device, comprising:
a handle graspable by a user and having a lower leaf extending from a forward end thereof to a distal end;
a lever pivotally coupled to the handle;
at least one upper leaf hingedly coupled to the handle and pivotable relative to the handle using the lever; and
a lock operably coupled to the handle and the lever, the lock comprising,
   a post depending from the lever and extending through a hole and into the handle,
   a torsion spring having a first end and a second end and retained on the post by tension of the torsion spring and inhibiting movement of the post and the lever relative to the handle, and
   a wedge configured to engage the first end and the second end of the torsion spring upon movement of the wedge to release the tension of the torsion spring and allow movement of the post and the lever relative to the handle;
wherein the lower leaf and the at least one upper leaf, in a collapsed configuration, are configured to be inserted into a vagina of a patient, expanded, and locked into an open position or the collapsed position using the lock.

14. The medical device of claim 13, further comprising a button configured for the movement of the wedge to wedge open the first end and the second end of the torsion spring.

15. The medical device of claim 14, wherein the button is operably coupled to the wedge.

16. The medical device of claim 14, wherein the button is integrally formed with the wedge.

17. The medical device of claim 13, wherein the wedge includes a slot configured to receive the post and the torsion spring retained on the post upon the movement of the wedge to release the tension of the torsion spring.

18. The medical device of claim 13, wherein the lever includes a pin configured to engage a slot in the at least one upper leaf, wherein movement of the pin in the slot pivots the at least one upper leaf relative to the handle.

\* \* \* \* \*